United States Patent
Li et al.

(10) Patent No.: US 12,156,928 B2
(45) Date of Patent: Dec. 3, 2024

(54) ANTIPERSPIRANT COMPOSITION COMPRISING INORGANIC POLYIONIC CLUSTER

(71) Applicant: Conopco, Inc., Trumbull, CT (US)

(72) Inventors: Xiaoke Li, Shanghai (CN); Renjiang Liu, Shanghai (CN); Yuekui Sun, Shanghai (CN); Jinfang Wang, Shanghai (CN); Meili Zhang, Taringa (AU); Huanjun Zhou, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 587 days.

(21) Appl. No.: 17/415,272

(22) PCT Filed: Dec. 20, 2019

(86) PCT No.: PCT/EP2019/086668
§ 371 (c)(1),
(2) Date: Jun. 17, 2021

(87) PCT Pub. No.: WO2020/144056
PCT Pub. Date: Jul. 16, 2020

(65) Prior Publication Data
US 2022/0054374 A1  Feb. 24, 2022

(30) Foreign Application Priority Data

Jan. 11, 2019 (WO) ................ PCT/CN2019/071360
Feb. 5, 2019 (EP) ..................................... 19155563

(51) Int. Cl.
| | | |
|---|---|---|
| A61K 8/24 | (2006.01) |
| A61K 8/04 | (2006.01) |
| A61K 8/34 | (2006.01) |
| A61K 8/58 | (2006.01) |
| A61K 8/92 | (2006.01) |
| A61Q 15/00 | (2006.01) |

(52) U.S. Cl.
CPC ................ *A61K 8/24* (2013.01); *A61K 8/046* (2013.01); *A61K 8/34* (2013.01); *A61K 8/58* (2013.01); *A61K 8/585* (2013.01); *A61K 8/92* (2013.01); *A61Q 15/00* (2013.01); *A61K 2800/31* (2013.01); *A61K 2800/524* (2013.01); *A61K 2800/805* (2013.01); *A61K 2800/874* (2013.01)

(58) Field of Classification Search
None
See application file for complete search history.

(56) References Cited

FOREIGN PATENT DOCUMENTS

| | | |
|---|---|---|
| CN | 107215885 | 9/2017 |
| CN | 107343857 | 11/2017 |
| EP | 0545556 | 6/1993 |
| JP | H11278816 | 10/1999 |
| JP | 2000219505 | 8/2000 |
| WO | WO0152805 | 7/2001 |
| WO | WO2013013903 | 1/2013 |

OTHER PUBLICATIONS

Search Report and Written Opinion in EP1915563; Apr. 1, 2019; European Patent Office (EPO).
Search Report and Written Opinion PCTEP2019086668; Mar. 12, 2020; World Intellectual Property Org. (WIPO).
Zhaoming Liu et al.; Crosslinking ionic oligomers as conformable precursors to calcium carbonate; Nature; 2019; pp. 394-398, XP093149110; 574.

*Primary Examiner* — Sin J Lee
(74) *Attorney, Agent, or Firm* — Stephanie Huang

(57) ABSTRACT

The present invention is in the field of antiperspirant compositions, in particular, compositions comprising antiperspirant actives. Disclosed is an anhydrous antiperspirant composition comprising an inorganic polyionic cluster having structure of (I) or (II); where M is Ca or Mg; and wherein the composition is substantially free of abrasives, which means less than 3.0% by weight of the composition; wherein anhydrous means the water content of the composition is less than 3.0%.

20 Claims, No Drawings

ANTIPERSPIRANT COMPOSITION COMPRISING INORGANIC POLYIONIC CLUSTER

CROSS REFERENCE TO RELATED APPLICATIONS

The present application is a U.S. National Phase Application under 35 U.S.C. § 371 of International Application No. PCT/EP2019/086668, filed on Dec. 20, 2019, which claims priority to International Application No. PCT/CN2019/071360, filed on Jan. 11, 2019, and European Patent Application No. 19155563.0, filed on Feb. 5, 2019, the contents of which are incorporated herein in their entireties.

FIELD OF THE INVENTION

The present invention is in the field of antiperspirant compositions.

BACKGROUND OF THE INVENTION

The present invention relates to compositions that contain antiperspirant actives. These actives are added to compositions to reduce perspiration upon topical application of the compositions to the body, particularly to the underarm regions of the human body viz. the axilla, and sometimes even on the upper part of the body near the chest.

Usually, conventional antiperspirant actives are salts of certain metals having an astringent effect, such as the salts of aluminium and/or zirconium. Since antiperspirants are used regularly, and have been used for decades, there is an ever-increasing need to develop alternative antiperspirant actives which are equally efficacious and safe.

Inorganic polyionic clusters have been recently developed for use in other areas of technology.

CN 107343857 A (Zhejiang University, 2017) discloses hydroxyapatite with an enamel-like structure and a method for preparing of the hydroxyapatite. A calcium phosphate polyionic cluster is taken as a precursor, and the hydroxyapatite with the enamel-like structure is prepared on the enamel surfaces through the precursor.

CN 107215885 A (Zhejiang University, 2017) discloses a method for preparing an inorganic polyionic cluster. The method comprises the following steps: dissolving an inorganic salt in a solvent with a relative dielectric constant less than or equal to 35, and by taking a small organic molecule amine compound as an end-capping reagent, adding inorganic acid or organic acid, standing by and centrifugally separating.

SUMMARY OF THE INVENTION

The present inventors have found that inorganic polyionic clusters are stable in a medium so long as the medium is substantially free of water. In addition to being stable under the conditions disclosed herein above, particles of the clusters are capable of forming a precipitation/aggregation when they contact with sweat/perspiration or after solvents in the carrier evaporate. Therefore, such a phenomenon of precipitation/aggregation can be used to block sweat ducts, partially or fully, in a non-permanent manner to inhibit sweating or perspiration. Therefore, the inorganic polyionic clusters can be used as actives in antiperspirant compositions, either by themselves or in combination with other conventional actives like compounds of aluminum such as ACH or zirconium. Their use in combination with other conventional actives could provide a useful technical route to reduce the reliance on conventional aluminum or zirconium based actives in such compositions.

In accordance with a first aspect is disclosed an anhydrous antiperspirant composition comprising an inorganic polyionic cluster having the structure of (I) or (II);

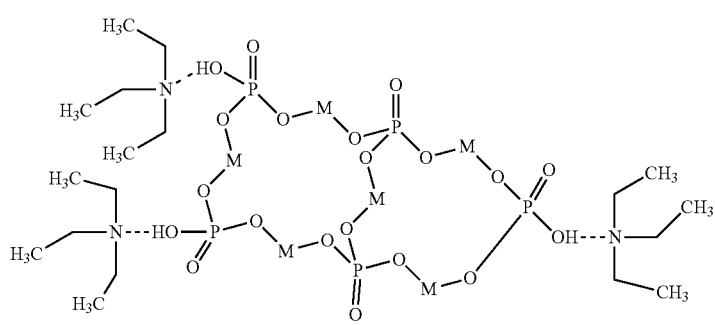

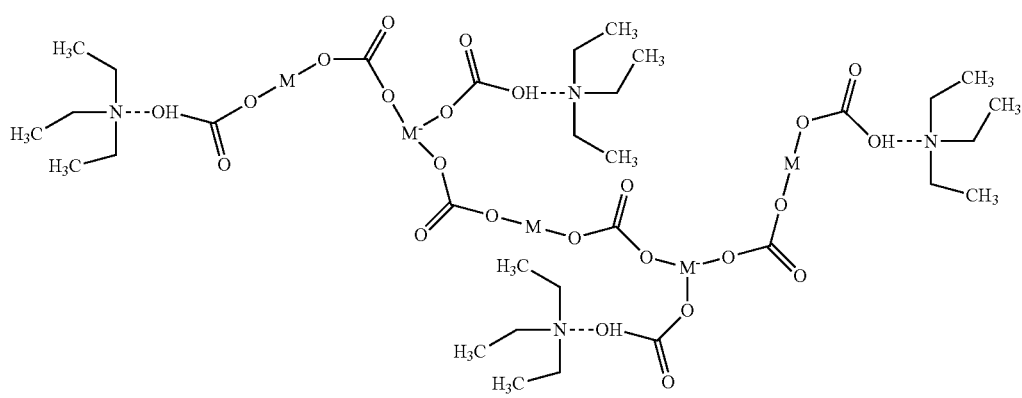

where M is Ca or Mg; and wherein the composition is substantially free of abrasives;
which means less than 3.0% by weight of the composition; wherein anhydrous means the water content of the composition is less than 3.0%.

In accordance with a second aspect is disclosed a method of reducing perspiration comprising a step of topical application of the composition of the first aspect.

In accordance with a third aspect is disclosed use of the composition of the first aspect for reduction of bodily perspiration In accordance with a fourth aspect is disclosed an anhydrous antiperspirant composition comprising an inorganic polyionic cluster, having structure of (I) or (II);

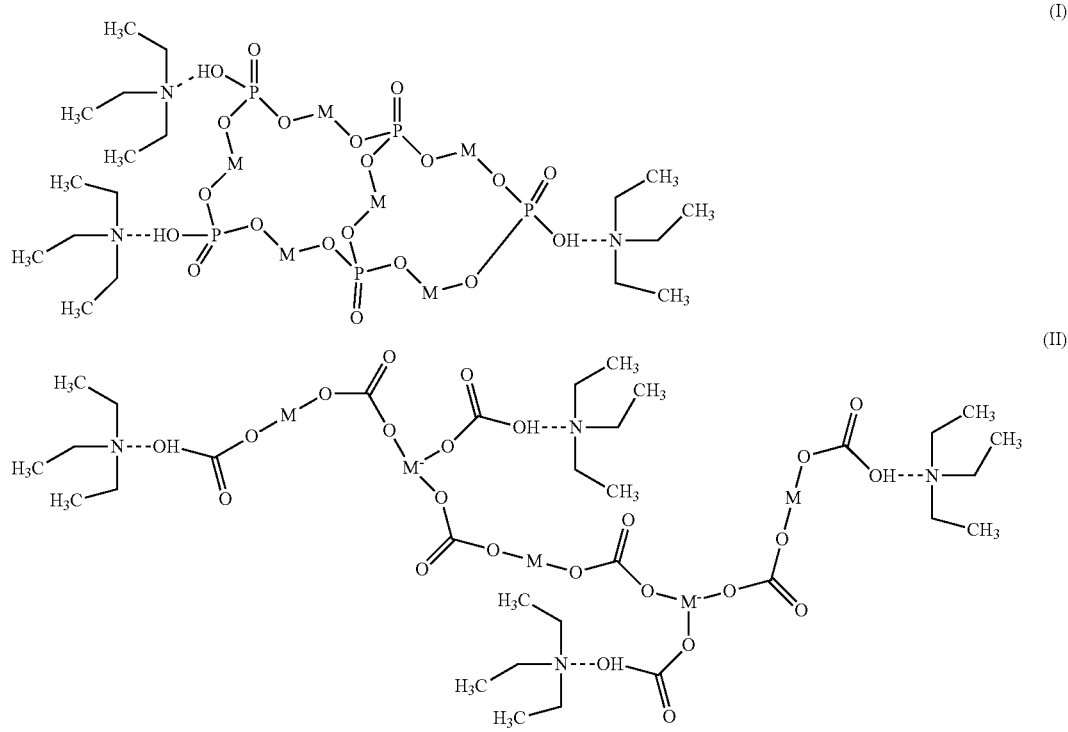

where M is Ca or Mg wherein said cluster is obtained by a process comprising the steps of:
  i) dissolving a water-soluble compound of calcium or a magnesium in ethanol to produce an ethanolic solution A having a calcium or magnesium ion concentration from 5 to 60 mmol/L;
  ii) dissolving triethylamine and phosphoric acid or carbonic acid in ethanol to produce an ethanolic solution B having phosphoric acid or carbonic acid concentration from 10 to 120 mmol/L and triethylamine concentration from 1000 to 3900 mmol/L;
  iii) mixing the solution A with the solution B and standing the mixture to obtain an inorganic polyionic cluster in solution form;
  iv) centrifuging the solution to obtain the inorganic polyionic cluster;
  wherein the composition is substantially free of abrasives which means less than 3.0% by weight of the composition; wherein anhydrous means the water content of the composition is less than 3.0%.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the antiperspirant composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION OF THE INVENTION

By "An antiperspirant Composition" as used herein, is meant to include a composition for topical application to the skin of mammals, especially humans. Such a composition is preferably of the leave-on type. By a leave-on composition is meant a composition that is applied to the desired skin surface and left on for one minute to 24 hours after which it may be wiped or rinsed off with water, usually during the regular course of personal washing. The composition may also be formulated into a product which is applied to a human body for improving the appearance, cleansing, odor control or general aesthetics. The composition of the present invention can be in the form of a liquid, lotion, cream, gel or stick form and may be delivered through a roll-on device or using an aerosol can which contains a propellant. "Skin" as used herein is meant to include skin on any part of the body (e.g., neck, chest, back, arms, underarms, hands, legs, buttocks and scalp) especially the underarms.

Solubility

"Soluble" and "insoluble" for the purpose of the present invention means the solubility of a source (e.g., like calcium salts) in water at 25° C. and atmospheric pressure. "Soluble" means a source that dissolves in water to give a solution with a concentration of at least 0.1 moles per litre. "Insoluble" means a source that dissolves in water to give a solution with a concentration of less than 0.001 moles per litre. "Slightly soluble", therefore, is defined to mean a source that dissolves in water to give a solution with a concentration of greater than 0.001 moles per litre and less than 0.1 moles per litre.

Substantially Free of Abrasives

"Substantially free of" for the purpose of the present invention means less than 3.0%, and preferably less than 2.0%, and more preferably less than 1.0% and most preferably less than 0.5% by weight of the antiperspirant composition.

Abrasives here mean the abrasives used in oral care compositions, for example, silica and calcium-based abrasives, especially chalk.

Anhydrous Composition

"Anhydrous composition" for the purpose of the present invention means the water content of the composition is less than 3.0%, and preferably less than 2.0%, and more preferably less than 1.0% and most preferably less than 0.5% by total weight of the antiperspirant composition.

Inorganic Polyionic Cluster

The inorganic polyionic cluster, as used herein, means nano-scale locally-branched linear polyionic clusters having certain degree of fluidity. The structure of inorganic polyionic cluster is similar to polymers but clusters are formed by ionic bonding and are completely composed of ions.

In the anhydrous antiperspirant composition of the invention, the inorganic polyionic cluster has the structure of (I) or (II):

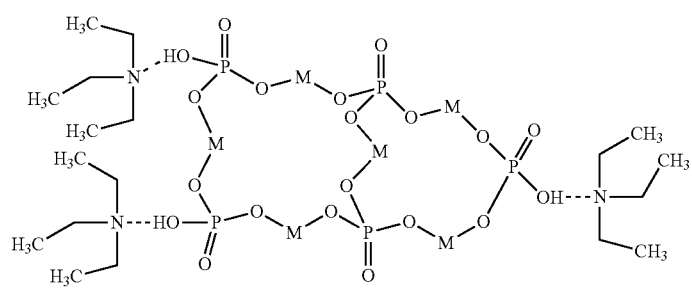

(I)

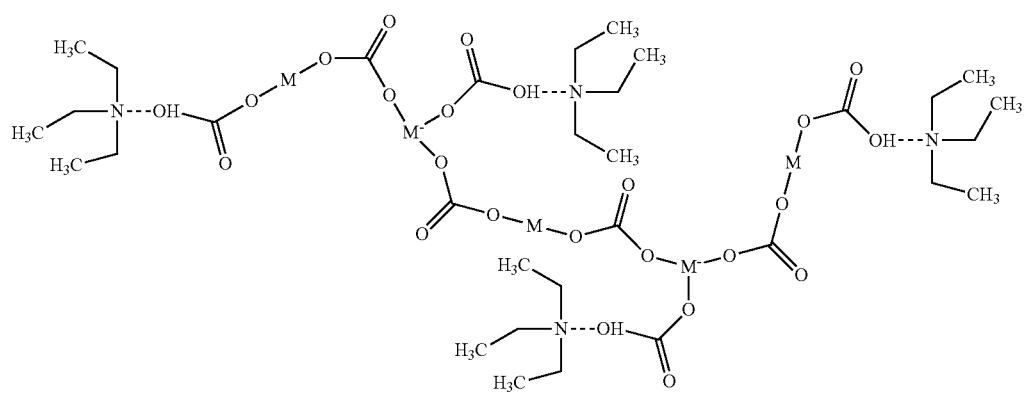

(II)

where M is Ca or Mg.

It is preferred that the inorganic polyionic cluster has the structure of (I). It is particularly preferred that in said structure of the formula (I), the M is calcium.

The inorganic polyionic clusters for use in this invention are preferably obtained by a process comprising the steps of:
i) dissolving a water-soluble compound of calcium or a magnesium in ethanol to produce an ethanolic solution A having a calcium or magnesium ion concentration from 5 to 60 mmol/L;
ii) dissolving triethylamine and phosphoric acid or carbonic acid in ethanol to produce an ethanolic solution B having phosphoric acid or carbonic acid concentration from 10 to 120 mmol/L and triethylamine concentration from 1000 to 3900 mmol/L;
iii) mixing the solution A with the solution B and standing the mixture to obtain an inorganic polyionic cluster in solution form;
iv) centrifuging the solution to obtain the inorganic polyionic cluster.

When ethanolic solution of carbonic acid is used in the step ii), the carbonic acid is introduced into the ethanolic solution by bubbling the $CO_2$ into the solution while stirring. It is preferred that the 100 ml/minute of $CO_2$ is bubbled into the solution and kept bubbling for 10 minutes.

The water-soluble calcium source provides calcium ions for the calcium phosphate/carbonate polyionic clusters. Illustrative, yet non-limiting examples include calcium chloride, calcium nitrate, calcium acetate, calcium lactate, calcium formate, calcium malate, calcium propionate, calcium butyrate, calcium bicarbonate, calcium glycerophosphate, calcium gluconate, calcium ascorbate or mixtures thereof. Preferably, the calcium source is calcium chloride.

The water-soluble magnesium source provides magnesium ions for the magnesium phosphate/carbonate polyionic clusters. Illustrative, yet non-limiting examples include magnesium chloride, magnesium nitrate and magnesium sulphate or mixtures thereof. Preferably, the magnesium source is magnesium chloride.

The ethanol solution A preferably has a calcium or magnesium ion concentration from 10 to 50 mmol/L, more preferably from 15 to 40 mmol/L. If the concentration of calcium/magnesium ion is too low, it will reduce the yield and waste the ethanol solvent. If the concentration of calcium is too high, it will rapidly form the polyionic clusters, resulting in non-uniform reaction.

The phosphoric acid or carbonic acid provides the phosphate anion or carbonate anion for the inorganic polyionic clusters. The ethanol solution B preferably has a phosphoric acid or carbonic acid concentration from 20 to 100 mmol/L, more preferably from 30 to 80 mmol/L. The triethylamine absorbs some of the protons in the phosphoric acid or carbonic acid as a base and it also behaves as a capping agent for the inorganic polyionic clusters formed. The ethanol solution B preferably has a triethylamine concentration from 1100 to 3000 mmol/L, more preferably from 1200 to 2500 mmol/L.

The solution A and the solution B are mixed and allowed to stand for some time to obtain an inorganic polyionic cluster solution. Typically, the solution A and the solution B are mixed in a volume ratio of from 1:1 to 10:1, more preferably from 2:1 to 10:1 and most preferably from 2:1 to 5:1. The standing time is preferably from 10 to 180 minutes, more preferably from 15 to 120 minutes, and most preferably from 20 to 60 minutes.

The inorganic polyionic clusters with fluidity are obtained by separating part of the ethanol solvent through centrifugation of the inorganic polyionic cluster solution. The fluidity of the clusters can be adjusted by the centrifugation speed and time. The higher the centrifugation speed and the longer the centrifugation time, the more viscous the clusters are. Typically, the centrifugation speed is from 5000 to 30000 rpm, more preferably from 6000 to 25000 rpm, and most preferably from 7000 to 22000 rpm. The centrifugation time is preferably from 1 to 80 minutes, more preferably from 1 to 30 minutes and most preferably from 3 to 10 minutes. In a preferred embodiment, the centrifugation speed is from 7000 to 22000 rpm, and the centrifugation time is from 3 to 10 minutes.

It is preferred that the antiperspirant composition comprises from 0.1 to 70 wt %, and more preferably from 1 to 50 wt %, and most preferably from 5 to 30 wt % the inorganic polyionic cluster, based on total weight of the composition.

Antiperspirant compositions in accordance with this invention may advantageously comprise an additional antiperspirant active. Whilst this could be a conventional antiperspirant salt comprising Al and/or other forms of Zr, such as aluminum chlorohydrate or aluminum-zirconium chlorohydrate optionally complexed with glycine, it is preferred that if any additional antiperspirant active is comprised in the compositions of the invention, is not of this type.

Without wishing to be bound by theory the inventors believe that It is essential to have the composition formulated with anhydrous carrier for the formulation to be stable, effective and safer to use. Once inside the sweat glands, it is believed that due to the contact with sweat/perspiration or the evaporation of solvents, the inorganic polyionic clusters tend to form precipitations/aggregations to thereby partially or fully, and in a non-permanent manner, clogs or blocks the sweat ducts to provide antiperspirant benefits.

Other Ingredients

Other components commonly included in conventional antiperspirant compositions may also be incorporated in the compositions of the present invention. Such components include skin care agents such as emollients, humectants and skin barrier promoters; skin appearance modifiers such as skin lightening agents and skin smoothing agents; anti-microbial agents, in particular organic anti-microbial agents, and preservatives.

The antiperspirant compositions of the invention are applied cosmetically and topically to the skin, broadly speaking, by one of two methods. Different consumers prefer one method or the other. In one method, sometimes called a contact method, the composition is wiped across the surface of the skin, depositing a fraction of the composition as it passes. In the second method, sometimes called the non-contact method, the composition is sprayed from a dispenser held proximate to the skin, often in an area of about 10 to 20 $cm^2$. The spray can be developed by mechanical means of generating pressure on the contents of a dispenser, such as a pump or a squeezable sidewall or by internally generated pressure arising from a fraction of a liquefied propellant volatilizing, the dispenser commonly being called an aerosol.

There are broadly speaking two classes of contact compositions, one of which is liquid and usually applied using a roll-on dispenser or possibly absorbed into or onto a wipe, and in the second of which the antiperspirant active is distributed within a carrier liquid that forms a continuous phase that has been gelled. In one variation, the carrier fluid comprises a solvent for the antiperspirant and in a second variation, the antiperspirant remains a particulate solid that is suspended in an oil, usually a blend of oils.

The composition of the invention is anhydrous and comprises cosmetically acceptable carrier.

The present invention also provides for an anhydrous antiperspirant composition comprising an inorganic polyionic cluster having structure of (I) or (II), wherein the composition is substantially free of abrasives, where said inorganic polyionic cluster is obtained by a process comprising the steps of:
  i) dissolving a water-soluble compound of calcium or a magnesium in ethanol to produce an ethanolic solution A having a calcium or magnesium ion concentration from 5 to 60 mmol/L;
  ii) dissolving triethylamine and phosphoric acid or carbonic acid in ethanol to produce an ethanolic solution B having phosphoric acid or carbonic acid concentration from 10 to 120 mmol/L and triethylamine concentration from 1000 to 3900 mmol/L;
  iii) mixing the solution A with the solution B and standing the mixture to obtain an inorganic polyionic cluster in solution form;

iv) centrifuging the solution to obtain the inorganic polyionic cluster.

When ethanolic solution of carbonic acid is used in the step ii), the carbonic acid is introduced into the ethanolic solution by bubbling the $CO_2$ into the solution while stirring. It is preferred that the 100 ml/minute of $CO_2$ is bubbled into the solution and kept bubbling for 10 minutes.

The present invention also provides for an anhydrous antiperspirant composition comprising an inorganic polyionic cluster, having structure of (I) or (II);

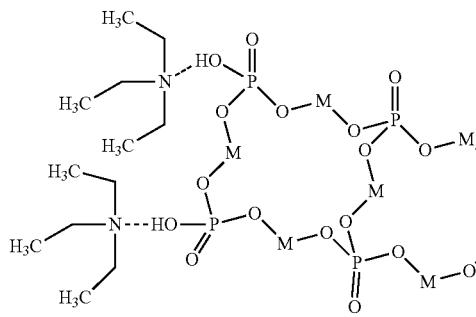

(I)

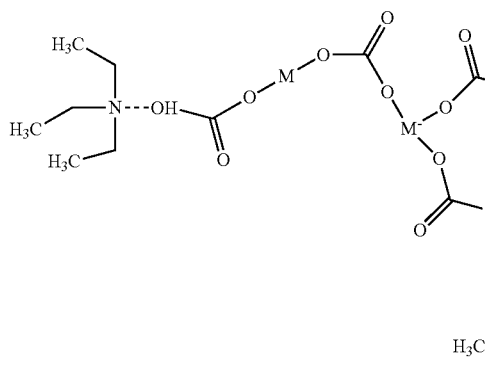

(II)

where M is Ca or Mg wherein said cluster is obtained by a process comprising the steps of:
i) dissolving a water-soluble compound of calcium or a magnesium in ethanol to produce an ethanolic solution A having a calcium or magnesium ion concentration from 5 to 60 mmol/L;
ii) dissolving triethylamine and phosphoric acid or carbonic acid in ethanol to produce an ethanolic solution B having phosphoric acid or carbonic acid concentration from 10 to 120 mmol/L and triethylamine concentration from 1000 to 3900 mmol/L;
iii) mixing the solution A with the solution B and standing the mixture to obtain an inorganic polyionic cluster in solution form;
iv) centrifuging the solution to obtain the inorganic polyionic cluster;
wherein the composition is substantially free of abrasives.

When ethanolic solution of carbonic acid is used in the step ii), the carbonic acid is introduced into the ethanolic solution by bubbling the $CO_2$ into the solution while stirring. It is preferred that the 100 ml/minute of $CO_2$ is bubbled into the solution and kept bubbling for 10 minutes.

It is preferred that the composition of the invention is in the form of a cream, a spray, a firm solid, a soft solid or is an emulsion packaged in a roll-on applicator.

Further preferably, when said composition is a spray it comprises a propellant and the composition is in the form of an aerosol.

Stick Compositions

In one aspect, the antiperspirant composition of the invention is a stick composition which is usually in the form of an emulsion.

Antiperspirant emulsion sticks can be formulated as clear (i.e., translucent or transparent) or opaque compositions. Translucent or transparent emulsion sticks go on clear and, depending upon their formulation, may remain clear for extended periods of time, reducing the consumer perceived negative of "white marks" associated with deposition of antiperspirant active. Many different materials have been proposed as gellants for a continuous oil phase, including waxes, small molecule gelling agents and polymers. They each have their advantages and of them, one of the most popular class of gellants is waxes, partly at least due to their ready availability and ease of processing, including in particular linear fatty alcohol wax gellants. A gelled antiperspirant composition is applied topically to skin by wiping it across and in contact with the skin, thereby depositing on the skin a thin film.

The nature of the film depends to a significant extent on the gellant that is employed. Although wax fatty alcohols have been employed as gellants for many years, and are effective for the purpose of gelling, the resultant product is rather ineffective at improving the visual appearance of skin, and in particular underarm skin, to which the composition has been applied. This problem has been solved by including ameliorating materials for example, di or polyhydric humectants and/or a triglyceride oil.

Stick compositions are usually available in the form of a firm solid or a soft solid. Firm solids, as the name indicates, are harder and can be directly applied by way of an applicator, for example, to the underarms. Soft solids also need an applicator which is similar to the firm solids, the difference being that the soft solids are softer and the applicator needs to be designed in order to permit extrusion of the solids through a cap member comprising plurality of orifices and the extruded composition can then be applied to the underarms.

Roll-On

Alternatively, the composition of the invention is a liquid composition, that can be dispensed from a roll-on package. Broadly speaking such compositions could be divided into two classes, namely those in which an antiperspirant active is suspended in a hydrophobic carrier, such as a volatile silicone and those in which the antiperspirant active is dissolved in a carrier liquid, such as glycerin and propylene glycol.

Aerosol Compositions

Further alternatively, the antiperspirant composition of the invention is delivered through an aerosol composition which comprises a propellant in addition to the applicable other ingredients described hereinabove. Commonly, the propellant is employed in a weight ratio to the base formulation of from 95:5 to 5:95. Depending on the propellant, in such aerosol compositions the ratio of propellant to base formulation is normally at least 20:80, generally at least 30:70, particularly at least 40:60, and in many formulations, the weight ratio is from 90:10 to 50:50. A ratio range of from 70:30 to 90:10 is sometimes preferred.

Propellants herein generally are one of three classes; (i) low boiling-point gasses liquified by compression, (ii) volatile ethers and (iii) compressed non-oxidising gases.

Class (i) is conveniently a low boiling-point material, typically boiling below −5° C., and often below −15° C., and in particular, alkanes and/or halogenated hydrocarbons. This class of propellant is usually liquefied at the pressure in the aerosol canister and evaporates to generate the pressure to expel the composition out of the canister. Examples of suitable alkanes include particularly propane, butane or isobutane. The class (ii) of propellant comprises a very volatile ether of which the most widely employed ether hitherto is dimethyl ether. This propellant can advantageously be employed at relatively low weight ratio of propellant to base formulation, for example to as low as 5:95. It can also be employed in admixture with, for example, compressible/liquefiable alkane gasses. The class (iii) of propellant comprises compressed non-oxidising gasses, and in particular carbon dioxide or nitrogen. Inert gases like neon are a theoretical alternative.

The composition of the present invention can comprise a wide range of other optional components. The CTFA Personal Care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, conditioners, exfoliating agents, pH adjusters, other than the ones already discussed earlier, preservatives, natural extracts, essential oils, skin sensates, skin soothing agents, and skin healing agents.

A preservative is a preferred additional component in compositions of the invention. A preservative serves to reduce or eliminate microbial contamination of compositions of the invention. Preservatives are typically employed at a total level of from 0.05 to 3%, preferably at from 0.1 to 2% and most preferably at from 0.4 to 1%.

Suitable preservatives for use with the present invention include 2-phenoxyethanol, iodopropynyl butylcarbamate, $C_1$-$C_3$ alkyl parabens, sodium benzoate, caprylyl glycol and EDTA. Particularly preferred preservatives are 2-phenoxyethanol, iodopropynyl butylcarbamate, sodium benzoate, caprylyl glycol and EDTA and especially preferred are 2-phenoxyethanol and iodopropynyl butylcarbamate.

A preferred additional component of compositions of the invention is a fragrance. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight.

An antimicrobial deodorant active is a preferred an additional component in compositions of the invention. Such components serve to reduce or eliminate body odour by reducing or otherwise impeding the function of microbes on the skin of the body responsible for malodour generation.

The antimicrobial deodorant active may also be a preservative for the composition.

When employed, the anti-microbial deodorant agent is typically incorporated into the composition at from 0.01% to 3% and particularly at from 0.03% to 0.5%.

Preferred anti-microbial deodorant agents have a minimum inhibitory concentration (MIC) of 1 mg·ml$^{-1}$ or less, particularly 200 µg·ml$^{-1}$ or less, and especially 100 µg·ml$^{-1}$ or less. The MIC of an anti-microbial agent is the minimum concentration of the agent required to significantly inhibit microbial growth. Inhibition is considered "significant" if an 80% or greater reduction in the growth of an inoculum of *Staphylococcus epidermidis* is observed, relative to a control medium without an anti-microbial agent, over a period of 16 to 24 hours at 37° C. Details of suitable methods for determining MICs can be found in "Antimicrobial Agents and Susceptibility Testing", C. Thornsberry, (in "Manual of Clinical Microbiology", 5$^{th}$ Edition, Ed. A. Balows et al, American Society for Microbiology, Washington D.C., 1991). A particularly suitable method is the Macrobroth Dilution Method as described in Chapter 110 of above publication (pp. 1101-1111) by D. F. Sahm and J. A. Washington II. MICs of anti-microbials suitable for inclusion in the compositions of the invention are triclosan: 0.01-10 µg·ml$^{-1}$ (J. Regos et al., Dermatologica (1979), 158: 72-79) and farnesol: ca. 25 µg·ml$^{-1}$ (K. Sawano, T. Sato, and R. Hattori, Proceedings of the 17$^{th}$ IFSCC International Conference, Yokahama (1992) p. 210-232). By contrast ethanol and similar alkanols have MICs of greater than 1 mg·ml$^{-1}$.

Suitable organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred anti-microbials for use in the compositions of the invention are polyhexamethylene biguanide salts (also known as polyaminopropyl biguanide salts), an example being Cosmocil CQ™ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight of the composition and more preferably at 0.05-0.3%; and 3,7,11-trimethyldodeca-2,6,10-trienol (farnesol), preferably used at up to 1% by weight of the composition and more preferably at up to 0.5%.

Other suitable organic antimicrobial agents are transition metal chelators, as described in WO01/52805, for example. Transitional metal chelators having a binding coefficient for iron(III) of greater than $10^{26}$, for example diethylenetriaminepentaacetic acid and salts thereof are preferred.

Method and Use

The present invention also provides for a method of reducing perspiration comprising a step of topical application of the composition of the first aspect. Preferably, the present invention provides for a method wherein the composition of the first aspect is applied on the underarms. The present invention also provides for a method wherein the composition of the first aspect partially or fully blocks sweat ducts in a non-permanent manner. The method in accordance with the invention is preferably non-therapeutic. By non-therapeutic is meant that the method is cosmetic in nature.

The invention also provides for use of the composition of the first aspect for reduction of bodily perspiration. The use in accordance with the invention is preferably non-therapeutic in nature, more preferably cosmetic in nature. Preferably, the present invention provides for use of the composition of the first aspect for partially or fully blocking sweat ducts in a non-permanent manner.

The invention will now be demonstrated with the help of the following non-limiting examples.

EXAMPLES

Example 1: Precipitation/Aggregation Formation of Compositions Triggered by Water Preparation of Calcium Phosphate Polyionic Clusters 0.19 grams calcium chloride dihydrate was dissolved in ethanol to obtain a 17 mmol/L calcium chloride solution as ethanolic solution A. 0.426 grams concentrated phosphoric acid (85%) and 13.11 grams triethylamine were dissolved in ethanol to get another ethanolic solution B having a phosphoric acid concentration of 40 mmol/L and a triethylamine concentration of 1300 mmol/L. The solution A and the solution B were mixed in a volume ratio of 4:1 and allowed to stand for 30 minutes to obtain an ethanolic solution of calcium phosphate polyionic clusters as a solution C. The solution C was centrifuged at 20000 rpm for 5 minutes to obtain calcium phosphate polyionic clusters. The calcium phosphate polyionic clusters were dispersed in ethanol with concentration of 50 mmol/L (Dispersion D).

Method

The precipitation/aggregation of calcium phosphate clusters triggered by water was investigated by measuring the change particle size after mixing dispersion D with different amounts of water. Briefly, 2.5 ml Dispersion D was mixed with different amounts of water (100, 200, 300, 400 μl) for 2 minutes, then the particle size of the clusters therein was measured by Malvern Zetasizer Nano ZS at 25° C. Details are summarised in Table-1.

TABLE 1

| Reference No. | Dispersion D (Calcium phosphate polyionic clusters + ethanol) | Added water | Mean particle size (nm) |
|---|---|---|---|
| 1 | 2.5 ml | 0 | 983 |
| A | 2.5 ml | 100 μl | 2722 |
| B | 2.5 ml | 200 μl | 4825 |
| C | 2.5 ml | 300 μl | 10986 |
| D | 2.5 ml | 400 μl | Sedimentation (not applicable for measurement) |

The results (shown in the Table-1) demonstrate that precipitation/aggregation of calcium phosphate polyionic clusters (Composition Reference No. 1) can be triggered by small amounts of water, which indicates that calcium phosphate polyionic clusters are capable of forming a precipitation/aggregation inside our sweat ducts (triggered by the sweat which contains water).

A composition of a model ionic sweat (pH 6.9) is given below in Table-2:

TABLE 2

| Ingredient | wt % of total |
|---|---|
| Potassium Chloride | 0.0373 |
| Sodium Bicarbonate | 0.2025 |
| Sodium Chloride | 0.2098 |
| Ammonium Chloride | 0.0107 |
| Calcium Chloride | 0.0222 |
| Lactic Acid | 0.0901 |
| Urea | 0.0018 |
| Water | 99.4256 |

2 ml of the dispersion D (50 mmol/L calcium phosphate polyionic clusters in ethanol) was taken in a 5 ml glass vial and a capillary tube (~500 um diameter, 10 cm length) filled with the model ionic sweat was immersed (~2 cm below liquid level) in the dispersion D for about 1 hour. Afterwards, the capillary tube was removed and dried for 60 minutes at room temperature and then the morphology was observed under optical microscope (Leica™ DMi8). Another capillary tube filled with model ionic sweat without immersing in dispersion D was observed as control to identify differences, if any. Precipitation/aggregation was observed inside the capillary tube (mimicking the sweat duct) treated with calcium phosphate polyionic clusters. However, for the control experiment, no precipitation or aggregation was observed inside the capillary tube. The result indicates that the composition as per the invention (Composition Reference No. 1) is capable of forming an aggregation/precipitation inside sweat ducts but the rest of the compositions are not so capable.

Comparative Example

A comparative example-composition E as given in Table-3 was prepared according to the Example 4 of application WO 2013/013903 and it was simplified by replacing the other ingredients (solvents, thickener, etc) by dimethicone.

TABLE 3

| Ingredient | wt % of total |
|---|---|
| CaCl$_2$ dihydrate | 7 |
| Sodium bicarbonate | 3 |
| Dimethicone | 90 |

A capillary tube (~500 um diameter, 10 cm length) was filled with the model ionic sweat as described in the above, and then was immersed (~2 cm below liquid level) in the dispersion of the test sample-Composition E (10 g) in a glass vial for about 1 hour. Afterwards, the capillary tube was removed and dried for 60 minutes at room temperature and then the morphology was observed under optical microscope (Leica™ DM 2500P). The result indicates that the composition out of the invention (Composition E) is not capable of efficiently forming an aggregation/precipitation inside sweat ducts, only few particles could be observed for Composition E.

The invention claimed is:

1. An anhydrous antiperspirant composition comprising an inorganic polyionic cluster having structure of (I);

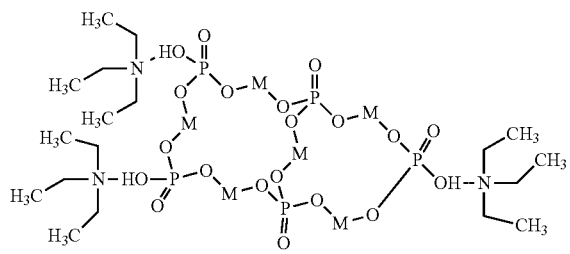

(I)

where M is Ca or Mg;
wherein the anhydrous antiperspirant composition comprises 0.1 to 70% by weight of the inorganic polyionic cluster;
wherein the anhydrous antiperspirant composition comprises less than 3.0% abrasive by weight of the composition; and
further wherein the anhydrous composition contains less than 3.0% water by weight of the composition.

2. The anhydrous antiperspirant composition as claimed in claim 1, wherein in the structure of (I), M is calcium.

3. The anhydrous antiperspirant composition as claimed in claim 1, wherein the composition comprises a silicone compound, a volatile alcohol or a wax.

4. The anhydrous antiperspirant composition as claimed in claim 1, wherein the composition comprises a fragrance.

5. The anhydrous antiperspirant composition as claimed in claim 1, wherein the composition comprises an antimicrobial deodorant.

6. The anhydrous antiperspirant composition as claimed in claim 1, wherein the composition comprises a preservative.

7. The anhydrous antiperspirant composition as claimed in claim 1, wherein the composition is in the form of a cream, a spray, a firm solid, a soft solid or is an emulsion packaged in a roll-on applicator.

8. The anhydrous antiperspirant composition as claimed in claim 7, wherein when the composition is a spray, it comprises a propellant and the composition is in the form of an aerosol.

9. A method of reducing perspiration comprising a step of topical application of the anhydrous antiperspirant composition as claimed in claim 1.

10. The method as claimed in claim 9, wherein the anhydrous antiperspirant composition partially or fully blocks sweat ducts in a non-permanent manner.

11. The anhydrous antiperspirant composition as claimed in claim 1, wherein the composition comprises an additional antiperspirant active that does not comprise aluminum and/or zirconium.

12. An anhydrous antiperspirant composition comprising an inorganic polyionic cluster having structure of (I);

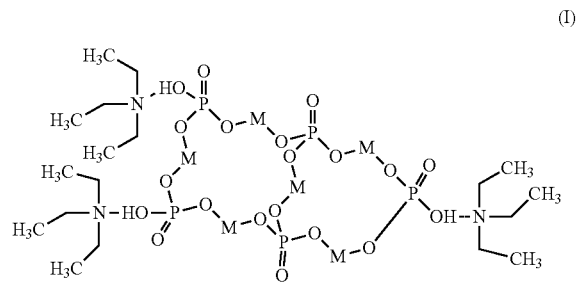

(I)

where M is Ca or Mg;
wherein the anhydrous antiperspirant composition comprises a fragrance, a preservative, or a combination thereof;
wherein the anhydrous antiperspirant composition comprises less than 3.0% abrasive by weight of the composition; and
further wherein the anhydrous composition contains less than 3.0% water by weight of the composition.

13. The anhydrous antiperspirant composition as claimed in claim 12, wherein in the structure of (I), M is calcium.

14. The anhydrous antiperspirant composition as claimed in claim 12, wherein the composition comprises 0.1 to 70% by weight of the inorganic polyionic cluster.

15. The anhydrous antiperspirant composition as claimed in claim 12, wherein the composition comprises a silicone compound, a volatile alcohol or a wax.

16. The anhydrous antiperspirant composition as claimed in claim 12, wherein the composition comprises an antimicrobial deodorant.

17. The anhydrous antiperspirant composition as claimed in claim 12, wherein the composition is in the form of a cream, a spray, a firm solid, a soft solid or is an emulsion packaged in a roll-on applicator.

18. The anhydrous antiperspirant composition as claimed in claim 17, wherein when the composition is a spray, it comprises a propellant and the composition is in the form of an aerosol.

19. A method of reducing perspiration comprising a step of topical application of the anhydrous antiperspirant composition as claimed in claim 12.

20. The method as claimed in claim 19, wherein the anhydrous antiperspirant composition partially or fully blocks sweat ducts in a non-permanent manner.

* * * * *